United States Patent

Stemp et al.

[11] Patent Number: 5,254,555
[45] Date of Patent: Oct. 19, 1993

[54] AMINO PYRIMIDIN-7-YL SUBSTITUTED BENZOPYRANS FOR TREATMENT OF HYPERTENSION

[75] Inventors: Geoffrey Stemp; John M. Evans, both of Harlow; Gordon Burrell, Swarthmoor, Nr. Ulverston, all of England

[73] Assignee: Beecham Group p.l.c., England

[21] Appl. No.: 855,446

[22] Filed: Mar. 19, 1992

Related U.S. Application Data

[63] Continuation of Ser. No. 604,873, Oct. 29, 1990, abandoned.

[30] Foreign Application Priority Data

Oct. 30, 1989 [GB] United Kingdom ............... 8924376

[51] Int. Cl.$^5$ ............... A61K 31/505; C07D 239/02; C07D 415/00; C07D 237/00
[52] U.S. Cl. ............... 514/256; 544/326; 544/328; 544/243; 544/230; 544/329
[58] Field of Search ............... 544/326, 328, 327, 243, 544/230, 329; 514/256

[56] References Cited

U.S. PATENT DOCUMENTS

| | | | |
|---|---|---|---|
| 3,624,084 | 11/1971 | Mathieu | 544/326 |
| 3,890,321 | 6/1975 | DeAngelis et al. | 544/327 |
| 3,978,055 | 8/1976 | Fauran et al. | 544/122 |
| 4,446,113 | 5/1984 | Evans et al. | 422/267 |
| 4,496,565 | 1/1985 | Evans et al. | 514/222 |
| 4,542,149 | 9/1985 | Evans et al. | 514/422 |
| 4,782,083 | 11/1988 | Cassidy et al. | 514/456 |
| 4,812,459 | 3/1989 | Evans et al. | 514/254 |
| 4,845,220 | 7/1989 | Altermatt | 544/294 |
| 4,925,839 | 5/1990 | Quagliato et al. | 514/212 |

FOREIGN PATENT DOCUMENTS 0415065 3/1991 Fed. Rep. of Germany.

Primary Examiner—Mukund J. Shah
Assistant Examiner—Matthew V. Grumbling
Attorney, Agent, or Firm—Rosenman & Colin

[57] ABSTRACT

Compounds of the formula (I) or pharmaceutically acceptable salts thereof

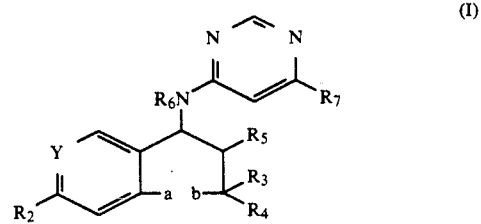

where $R_2$–$R_7$, Y, a and b are as defined, are useful in the treatment of hypertension and respiratory tract disorders.

10 Claims, No Drawings

AMINO PYRIMIDIN-7-YL SUBSTITUTED BENZOPYRANS FOR TREATMENT OF HYPERTENSION

This is a continuation of U.S. application Ser. No. 07/604,873 filed Oct. 29, 1990 now abandoned.

This invention relates to novel compounds having pharmacological activity, to a process for their preparation and to their use as pharmaceuticals.

EP-A-76075, 91748, 107423, 139992, 168619, 205292, 214818, 250077 and 321175 (Beecham Group p.l.c.), EP-A-314446 (American Home Products Corporation), EP-A-296975 (Sanofi) and WO 89/07103 (Nissan Chemical Industries Ltd.) describe benzopyran, tetrahydronaphthalene, pyranopyridine and indane derivatives possessing pharmacological activity, in particular, antihypertensive activity and/or bronchodilator activity.

EP-A-363883 (Merck Patent Gesellschaft, published 18.04.90) describes a group of benzopyrans having one of a number of 6-membered N-containing heterocycles linked through N or O, at the 4-position.

A novel group of compounds has now been discovered, which compounds have a substituted pyrimidineamino substituent at the 4- (or equivalent) position. These compounds have been found to have blood pressure lowering activity, useful in the treatment of hypertension, and bronchodilator activity, useful in the treatment of respiratory tract disorders. In addition, these compounds are believed to be K+ channel activators which indicates that they are of potential use in the treatment of disorders associated with smooth muscle contraction of the gastro-intestinal tract, respiratory system, uterus or urinary tract including the ureter. Such disorders include irritable bowel syndrome and diverticular disease; reversible airways obstruction including asthma; premature labour; and incontinence, renal cholic and disorders associated with kidney stones. They are also indicated as of potential use in the treatment of cardiovascular disorders other than hypertension, such as congestive heart failure, angina, peripheral vascular disease, cerebral vascular disease, pulmonary hypertension and right heart failure. K+ channel activators are also indicated as of potential use in the treatment of epilepsy and glaucoma.

Accordingly, the present invention provides a compound of formula (I) or a pharmaceutically acceptable salt thereof:

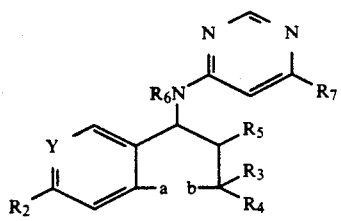

(I)

wherein
a and b together form an —O— or —CH$_2$— linkage or a bond;
either Y is N and R$_2$ is hydrogen; or
Y is C—R$_1$
wherein
either one of R$_1$ and R$_2$ is hydrogen and the other is nitro, cyano, halo, CF$_3$, C$_2$F$_5$, formyl, aldoxime, CF$_3$O, NO$_2$—CH=CH—, NC—CH=CH—; a group R$_x$X— wherein R$_x$ is C$_{1-6}$ alkyl, aryl or heteroaryl either of which may be optionally substituted by one, two or three of C$_{1-4}$ alkyl, C$_{1-4}$ alkoxy, nitro, halo, CF$_3$ and cyano; and X is C=O, O.C=O, C=O.O, CHOH, SO, SO$_2$, O.SO, O.SO$_2$, CONH, O.CONH, C=S, O.C=S, C=S.O, CH.SH, SONH, SO$_2$NH, O.SONH, O.SO$_2$NH, CO-CH=CH, C=NHOH, C=NNH$_2$; or a group R$_y$R$_z$NZ— wherein R$_y$ and R$_z$ are independently hydrogen or C$_{1-6}$ alkyl and Z is C=O, SO or SO$_2$; or a group (R$_w$O)$_2$P(O)W wherein R$_w$ is hydrogen or C$_{1-6}$ alkyl and W is O or a bond; or R$_1$ is a C$_{3-8}$ cycloalkyl group or a C$_{1-6}$ alkyl group optionally substituted by a group which is hydroxy, C$_{1-6}$ alkoxy, amino optionally substituted by one or two C$_{1-6}$ alkyl groups, C$_{1-7}$ alkanoylamino, C$_{3-8}$ cycloalkyloxy or C$_{3-8}$ cycloalkylamino; and R$_2$ is hydrogen; or one of R$_1$ and R$_2$ is nitro, cyano or C$_{1-3}$ alkylcarbonyl and the other is a different group selected from nitro, cyano, halo, C$_{1-3}$ alkylcarbonyl, methoxy or amino optionally substituted by one or two C$_{1-6}$ alkyl or by C$_{2-7}$ alkanoyl; or R$_1$ and R2 together with the carbon atoms to which they are attached, form 2,1,3-oxadiazole or triazole;
either one of R$_3$ and R$_4$ is hydrogen or C$_{1-4}$ alkyl and the other is C$_{1-4}$ alkyl; or
R$_3$ and R$_4$ together are C$_{2-5}$ polymethylene;
R$_5$ is hydrogen, hydroxy, C$_{1-6}$ alkoxy, C$_{1-7}$ acyloxy or ONO$_2$;
R$_6$ is hydrogen or C$_{1-6}$ alkyl; and
R$_7$ is halo, amino or methylamino.

The pyrimidineamino moiety is cis or trans to the R$_5$ group when R$_5$ is other than hydrogen, preferably trans.

In an alternative aspect of the invention, the aromatic ring containing Y may be replaced by optionally substituted thiophene, as described in EP-A-360621 (Ortho Pharmaceutical).

Preferably Y is N or C—R$_1$ and a and b together are an —O— linkage or Y is C—R$_1$ and a and b together are a bond or CH$_2$.

When either one of R$_1$ and R$_2$ is hydrogen, the other is preferably selected from halo, CF$_3$, C$_2$F$_5$, C$_{1-6}$ alkylcarbonyl, C$_{1-6}$ alkoxycarbonyl, nitro or cyano.

When one of R$_1$ and R$_2$ is nitro, cyano or C$_{1-3}$ alkylcarbonyl the other is, favourably, amino optionally substituted by one or two C$_{1-6}$ alkyl groups or by C$_{2-7}$ alkanoyl. In particular, when one of R$_1$ and R$_2$ is nitro, cyano or acetyl, the other is amino, methylamino, dimethylamino or acetylamino. Preferably, when one of R$_1$ and R$_2$ is nitro or cyano, especially cyano, the other is amino.

Halo substituents in R$_1$ and/or R$_2$ are usually chloro or bromo.

Alkyl groups in R$_1$/R$_2$ including R$_x$, R$_y$, R$_z$, R$_w$, are usually selected from methyl, ethyl, n- and iso-propyl, n, iso-, sec- and tert-butyl. Suitable examples of other alkyl or alkyl containing groups in R$_1$ and in R$_3$ and R$_4$ when alkyl include those listed for R$_1$ and R$_2$ alkyl containing groups. C$_{3-8}$ cycloalkyl includes C$_3$, C$_4$, C$_5$, C$_6$ cycloalkyl, in particular, cyclopentyl.

A sub-group of R$_x$ heteroaryl is 5- or 6-membered monocyclic or 9- or 10-membered bicyclic heteroaryl of which 5- or 6-membered monocyclic heteroaryl is preferred. In addition, 5- or 6-membered monocyclic or 9- or 10-membered bicyclic heteroaryl preferably contains one, two or three heteroatoms which are selected from the class of oxygen, nitrogen and sulphur and which, in the case of there being more than one heteroatom, are the same or different. Examples of 5- or 6-membered monocyclic heteroaryl containing one, two or three heteroatoms which are selected from the class of oxygen, nitrogen and sulphur include furyl, thienyl, pyrryl, oxazolyl, thiazolyl, imidazolyl and thiadiazolyl, and pyridyl, pyridazyl, pyrimidyl, pyrazyl and triazyl. Preferred examples of such groups include furanyl, thienyl, pyrryl and pyridyl, in particular 2- and 3-furyl, 2- and 3-pyrryl, 2- and 3-thienyl, and 2-, 3- and 4-pyridyl. Examples of 9- or 10-membered bicyclic heteroaryl containing one, two or three heteroatoms which are selected from the class of oxygen, nitrogen and sulphur include benzofuranyl, benzothienyl, indolyl and indazolyl, quinolyl and isoquinolyl, and quinazolinyl. Preferred examples of such groups include 2- and 3-benzofuryl, 2- and 3-benzothienyl, and 2- and 3-indolyl, and 2- and 3-quinolyl.

Preferred examples of the groups or atoms for optional substitution of $R_x$ when aryl or heteroaryl include methyl, methoxy, hydroxy, chloro, nitro or cyano.

$R_1$ is preferably nitro, cyano, acetyl, $CF_3$, $C_2F_5$, methyl, ethyl, isopropyl, t-butyl or cyclopentyl.

Preferably $R_3$ and $R_4$ are both methyl groups.

Suitable examples of $R_5$ when alkoxy include methoxy, ethoxy, n- and iso-propoxy, of which methoxy is preferred. When $R_5$ is $C_{1-7}$ acyloxy it is usually $C_{1-7}$ carboxylic acyloxy, such as $C_{1-7}$ alkanoyloxy wherein the alkyl moiety is usually as listed for alkyl in $R_1$ and $R_2$ above.

$R_5$ is favourably hydroxy or hydrogen, preferably hydroxy.

Suitable values for $R_6$ when $C_{1-6}$ alkyl include those values described for $R_1$ and $R_2$ alkyl moieties.

Examples of pharmaceutically acceptable salts include acid addition salts with acids such as hydrochloric, hydrobromic, phosphoric, sulphuric, citric, tartaric, lactic or acetic acid.

The compounds of formula (I) have at least one asymmetric centre and therefore exist in more than stereoisomeric form. The invention extends to each of these forms individually and to mixtures thereof, such as racemates.

The compounds of formula (I) and their salts may form solvates, such as hydrates, and these are included as part of the invention, wherever a compound of formula (I) or a salt thereof is herein referred to.

A preferred group of compounds within formula (I) is of formula (II):

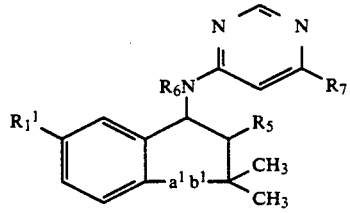

(II)

wherein $R_1^1$ is nitro, cyano, $CF_3$, $C_2F_5$, methyl, ethyl, isopropyl or acetyl, $a^1$ and $b^1$ together form an —O— linkage, a bond or $CH_2$; and $R_5$ to $R_7$ are as defined in formula (I).

Suitable and preferred values for the variables are as described for the corresponding variables in formula (I).

The invention provides a process for the preparation of a compound of formula (I) or a pharmaceutically acceptable salt thereof, which process comprises reacting a compound of formula (III):

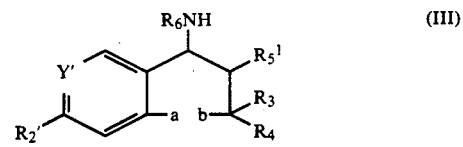

(III)

with a compound of formula (IV):

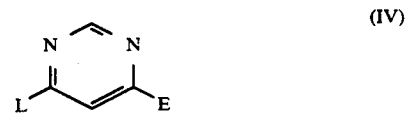

(IV)

wherein $R_5^1$ is hydroxy or hydrogen, L is a leaving group and E is a leaving group or $R_7$ as defined, and the remaining variables are as hereinbefore defined; and thereafter, when E is a leaving group, optionally reacting the resulting compound with ammonia or methylamine to give a compound of formula (I) wherein $R_7$ is $NH_2$ or $NHCH_3$, and optionally converting Y' and/or $R_2'$ to Y and/or $R_2$ as desired or necessary; when $R_5$ in formula (I) is other than hydrogen or hydroxy, converting an $R_5^1$ hydroxy group to other $R_5$; and thereafter optionally forming a pharmaceutically acceptable salt thereof.

Suitable values for E when a leaving group and L, include halo, such as chloro or bromo, preferably chloro. It will be appreciated that, when leaving group E is halo, the resulting compound is of formula (I).

The reaction preferably takes place in a solvent, such as ethanol, in the presence of a base, such as triethylamine, at elevated temperatures.

Preferably E is a leaving group, in which case the resulting compound of formula (V):

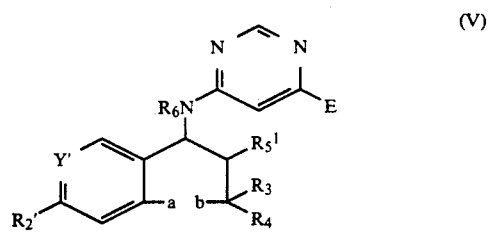

(V)

may be converted to a corresponding compound of formula (I) herein $R_7$ is $NH_2$ or $NHCH_3$, by reaction with ammonia or methylamine under conventional conditions. The reaction with ammonia may be achieved by heating in ethanol in an autoclave at elevated temperature, 50°–100° C.

Conversions of Y' to Y and $R_2'$ to $R_2$ are conventional in the art of aromatic chemistry.

Conversion of $R_5$ may be carried out as described in the aforementioned European Patent Publications.

Pharmaceutically acceptable salts may be formed conventionally.

Intermediates of the formula (III) wherein $R_5^1$ is hydroxy are known and may be prepared according to the methods described in U.S. Pat. Nos. 4,758,677, 4,446,113, 4,542,149, 4,800,212 and 4,181,2459 (Evans et. al.) and EP-A-205292, 214818, 250077 and 321175

(Beecham Group p.l.c.); or the other patent publications hereinbefore referred to.

Intermediates of formula (III) wherein $R_5^1$ is hydrogen, and $R_6$ is hydrogen may be prepared from intermediates of formula (VI) according to the following reaction scheme:

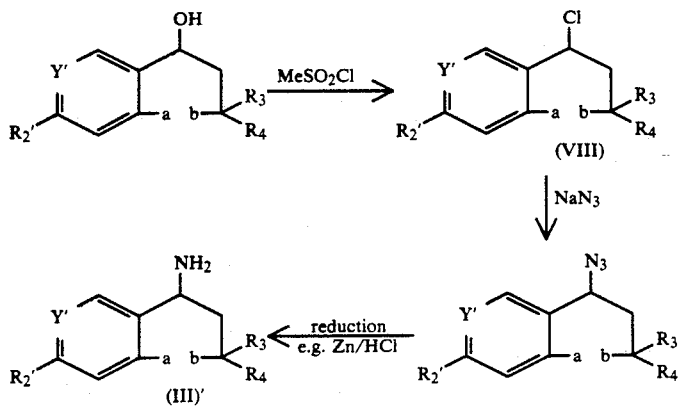

Intermediates of the formula (III) wherein $R_6$ is $C_{1-6}$ alkyl and $R_5^1$ is hydrogen may be prepared from intermediates of formula (III)' by convential amine alkylation or reductive amination methods, or from intermediates of formula (VIII) by reaction with $R_6NH_2$.

Intermediates of formula (VI) may be prepared according to the method described in GB 2204368A (Sandoz Limited).

Intermediates of the formula (IV) are known or are prepared by analogous methods to those used for structurally similar known compounds.

It will be appreciated that, when $R_5$ is other than hydrogen, it is preferred that the compound of formula (I) is isolated in the form of a pure single enantiomer, preferably the (3S,4R)- isomer. This may either be prepared by resolution or stereospecifically using resolved intermediates.

As mentioned previously, the compounds of formula (I) have been found to have blood-pressure lowering activity and bronchodilator activity. They are therefore useful in the treatment of hypertension and respiratory tract disorders. They are also believed to be of potential use in the treatment of other disorders hereinbefore referred to.

The present invention accordingly provides a pharmaceutical composition which comprises a compound of formula (I) or a pharmaceutically acceptable salt thereof, and a pharmaceutically acceptable carrier. In particular, the present invention provides an anti-hypertensive or bronchodilator pharmaceutical composition which comprises an effective amount of a compound of formula (I) or a pharmaceutically acceptable salt thereof, and a pharmaceutically acceptable carrier.

The compositions are preferably adapted for oral administration. However, they may be adapted for other modes of administration, for example parenteral administration for patients suffering from heart failure. Other alternative modes of administration include sublingual or transdermal administration. A composition may be in the form of spray, aerosol or other conventional method of inhalation, for treating respiratory tract disorders.

The compositions may be in the form of tablets, capsules, powders, granules, lozenges, suppositories, reconstitutable powders, or liquid preparations, such as oral or sterile parenteral solutions or suspensions.

In order to obtain consistency of administration it is preferred that a composition of the invention is in the form of a unit dose.

Unit dose presentation forms for oral administration may be tablets and capsules and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulphate.

The solid oral compositions may be prepared by conventional methods of blending, filling or tabletting. Repeated blending operations may be used to distribute the active agent throughout those compositions employing large quantities of fillers. Such operations are of course conventional in the art. The tablets may be coated according to methods well known in normal pharmaceutical practice, in particular with an enteric coating.

Oral liquid preparations may be in the form of, for example, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid; and if desired conventional flavouring or colouring agents.

For parenteral administration, fluid unit dosage forms are prepared utilizing the compound and a sterile vehicle and, depending on the concentration used, can be either suspended or dissolved in the vehicle. In preparing solutions the compound can be dissolved in water for injection and filter sterilized before filling into a suitable vial or ampoule and sealing. Advantageously, adjuvants such as a local anaesthetic, a preservative and buffering agents can be dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain from 0.1% to 99% by weight, preferably from 10–60% by weight, of the active material, depending on the method of administration.

The present invention further provides a method of prophylaxis or treatment of hypertension or respiratory tract disorders in mammals including man, which comprises administering to the suffering mammal an effective amount of a compound of formula (I) or a pharmaceutically acceptable salt thereof.

An effective amount will depend on the relative efficacy of the compound, the severity and nature of the disorder being treated and the weight of the sufferer. However, a unit dose form of a composition of the invention may contain from 0.05 to 500 mg of a compound of the invention and more usually from 0.1 to 50 mg, for example 0.5 to 25 mg such as 0.5, 1, 2, 5, 10, 15 or 20mg. Such compositions may be administered from 1 to 6 times a day, more usually from 1 to 4 times a day, in a manner such that the daily dose is from 0.01 to 25 mg for a per kg body weight and more particularly from 0.1 to 10 mg/kg.

No toxicological effects are indicated at the aforementioned dosage ranges.

The compounds of formula (I) and pharmaceutically acceptable salts thereof are believed to show a synergistic effect with ACE inhibitor or β-blocker antihypertensive agents and such combination products, for concomitant or sequential administration, are within the present invention.

The present invention further provides a compound of formula (I) or a pharmaceutically acceptable salt thereof for use in the treatment or prophylaxis of hypertension and/or respiratory tract disorders.

The following descriptions relate to the preparation of intermediates and the following examples relate to the preparation of compounds of formula (I).

EXAMPLE 1

Trans-6-Cyano-4-[(6-chloropyrimidin-4-yl)amino]-3,4-dihydro-2,2-dimethyl-2H-1-benzopyran-3-ol (E1)

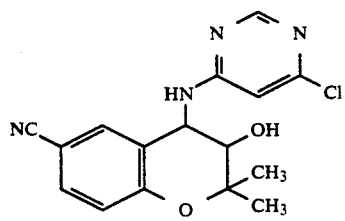

(E1)

A solution of trans-6-cyano-4-amino-3,4-dihydro-2,2-dimethyl-2H-1-benzopyran-3-ol (prepared as described in U.S. Pat. No. 4,446,113) (2.0 g) and 4,6-dichloropyrimidine (1.5 g) in ethanol (25 mL) and triethylamine (1.3 mL) was heated under reflux for 72 h. The solution was allowed to cool and the precipitate filtered off, and dissolved in ethyl acetate. The ethyl acetate solution was washed with water, 0.5N hydrochloric acid, sodium bicarbonate solution, brine, and then dried ($Na_2SO_4$). Removal of drying agent and solvent gave the title compound as a solid (1.08 g). A sample recrystallised from acetonitrile had m.pt. 204°–8° C.

$^1$H nmr ($CD_3OD$) δ 1.33 (s, 3H), 1.52 (s, 3H), 3.68 (d, J=10Hz, 1H), 5.30–5.40 (m, 1H), 6.62 (s, 1H), 6.90 (d, J=9Hz, 1H), 7.40–7.50 (m, 2H), 8.32 (s, 1H).

The (3S,4R)-enantiomer of the title compound was prepared analogously from the (3S,4R)-aminoalcohol, which is prepared as described in EP-A-384584 (Beecham Group p.l.c.). The compound had an optical rotation of −87.45°, c=0.55 MeOH.

EXAMPLE 2

Trans-6-Cyano-4-[(6-methylaminopyrimidin-4-yl)amino-3,4-dihydro-2,2-dimethyl-2H-1-benzopyran-3-ol

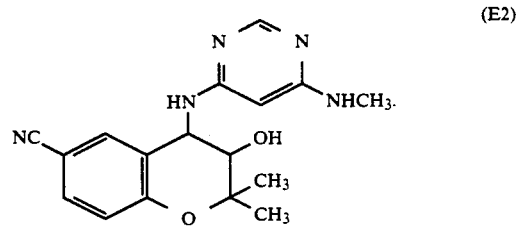

(E2)

The title compound was prepared from E1 by reaction with methylamine, according to the methods hereinbefore described m.pt. 226°–7° C.

EXAMPLE 3

Trans-6-Cyano-4-[(6-aminopyrimidin-4-yl)amino-3,4-dihydro-2,2-dimethyl-2H-1-benzopyran-3-ol

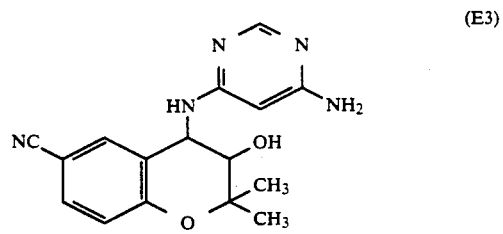

(E3)

The title compound was prepared from E1 by reacting with ammonia in ethanol in an autoclave, as hereinbefore described. Found M+ 311.1383, $C_{16}H_{17}N_5O_2$ requires M+ 311.1384.

PHARMACOLOGICAL DATA

1. Antihypertensive Activity

Systolic blood pressures were recorded by a modification of the tail cuff method described by I. M. Claxton, M. G. Palfreyman, R. H. Poyser, R. L. Whiting, European Journal of Pharmacology, 37, 179 (1976). A W+W BP recorder, model 8005 was used to display pulses. Prior to all measurements rats were placed in a heated environment (33.5±0.5° C.) before transfer to a restraining cage. Each determination of blood pressure was the mean of at least 5 readings. Spontaneously hypertensive rats (ages 12–18 weeks) with systolic blood pressures >180 mmHg were considered hypertensive.

2. Bronchodilator Activity

Male guinea pigs (300-600 g) were stunned by a blow to the head and bled from the carotid artery. The trachea was exposed, dissected free of connective tissue, and transferred to oxygenated Krebs solution at 37° C. Next, spirals (2 per trachea) were prepared by cutting the whole trachea spirally along its longitudinal axis and then dividing this spiral lengthwise. Each preparation was mounted, using silk thread, in a 10 ml organ bath filled with Krebs solution at 37° C. and bubbled with 5% $CO_2$ with $O_2$. The resting tension of the preparations was set at 2 g and changes in muscle tension were monitored isometrically by means of a UFI (2oz) force and displacement transducer (Ormed Ltd) connected to a Linseis pen recorder. All preparations were allowed to equilibrate for 60 minutes. During this equilibration period the preparations were washed by upward displacement at 15 minute intervals and, if necessary, the resting tension was readjusted to 2 g using a mechanical micromanipulator system.

Once a steady resting tension had been obtained, the preparations were dosed simultaneously with the test compound ($10^{-8}$-$2\times10^{-5}$M), and finally a maximum relaxation achieved by addition of $10^{-3}$M isoprenaline. The fall in tension evoked by the test compound was expressed as a percentage of the total relaxation evoked in the presence of $10^{-3}$ isoprenaline. Appropriate concentration-relaxation curves were then L constructed and values for potency ($IC_{50}$) were obtained.

The composition of Krebs solution is: sodium chloride 118.07 mM, sodium hydrogen carbonate 26.19 mM, potassium chloride 4.68 mM, potassium orthophosphate 1.18 mM, magnesium sulphate septahydrate 1.8 mM and calcium chloride 2.52 mM;pH ca. 7.45.]

The results in tests 1. and 2. were as follows:

| Compound | b.p. lower/dose | $IC_{50}$ |
| --- | --- | --- |
| E1 | 36%/0.3 mgkg$^{-1}$ | $1.5 \times 10^{-6}$M (n = 2) |
| E1* | 38%/0.15 mgkg$^{-1}$ | $5.1 \times 10^{-7}$M (n = 2) |

*(3S,4R)-enantiomer.

The compounds of Examples 2 and 3 were found to be active in tests 1. and 2.

We claim:

1. A compound of formula (I) or a pharmaceutically acceptable salt thereof:

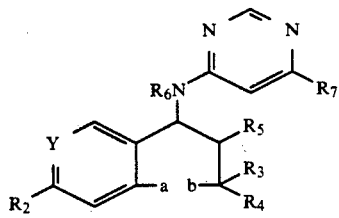

(I)

wherein
a and b together form an —O— or —$CH_2$— linkage or a bond;
either Y is N and $R_2$ is hydrogen; or
Y is C—$R_1$
wherein
either one of $R_1$ and $R_2$ is hydrogen and the other is nitro, cyano, halo, $CF_3$, $C_2F_5$, formyl, aldoxime, $CF_3O$, $NO_2$—CF=CH—, NC—CH= CH—; a group $R_xX$— wherein $R_x$ is $C_{1-6}$ alkyl, aryl or 2- or 3-furyl, 2- or 3-pyrryl, 2- or 3-thienyl, or 2-, 3- or 4-pyridyl, or 2- or 3-benzofuryl, 2- or 3-benzothienyl, or 2- or 3-indolyl, or 2- or 3-quinolyl, either of which may be optionally substituted by one, two or three of $C_{1-4}$ alkyl, $C_{1-4}$ alkoxy, nitro, halo, $CF_3$ and cyano; and X is C=O, O.C=O, C=O.O, CHOH, SO, $SO_2$, O.SO, O.$SO_2$, CONH, O.CONH, C=S, O.C=S, C=S.O, CH.SH, SONH, $SO_2$NH, O.-SONH, O.$SO_2$NH, CO—CH=CH, C=NHOH, C=$NNH_2$; or a group $R_yR_zNZ$— wherein $R_y$ and $R_z$ are independently hydrogen or $C_{1-6}$ alkyl and Z is C=O, SO or $SO_2$; or a group $(R_wO)_2$-P(O)W wherein $R_w$ is hydrogen or $C_{1-6}$ alkyl and W is O or a bond; or
$R_1$ is a $C_{3-8}$ cycloalkyl group or a $C_{1-6}$ alkyl group optionally substituted by a group which is hydroxy, $C_{1-6}$ alkoxy, amino optionally substituted by one or two $C_{1-6}$ alkyl groups, $C_{1-7}$ alkanoylamino, $C_{3-8}$ cycloalkyloxy or $C_{3-8}$ cycloalkylamino; and $R_2$ is hydrogen; or
one of $R_1$ and $R_2$ is nitro, cyano or $C_{1-3}$ alkylcarbonyl and the other is a different group selected from nitro, cyano, halo, $C_{1-3}$ alkylcarbonyl, methoxy or amino optionally substituted by one or two $C_{1-6}$ alkyl or by $C_{2-7}$ alkanoyl; or
$R_1$ and $R_2$ together with the carbon atoms to which they are attached, form 2,1,3-oxadiazole or triazole;
either one of $R_3$ and $R_4$ is hydrogen or $C_{1-4}$ alkyl and the other is $C_{1-4}$ alkyl; or
$R_3$ and $R_4$ together are $C_{2-5}$ polymethylene;
$R_5$ is hydrogen, hydroxy, $C_{1-6}$ alkoxy, $C_{1-7}$ acyloxy or $ONO_2$;
$R_6$ is hydrogen or $C_{1-6}$ alkyl; and
$R_7$ is halo, amino or methylamino.

2. A compound according to claim 1 wherein Y is C—$R_1$ and a and b together are an —O— linkage.

3. A compound according to claim 1 wherein $R_1$ is nitro, cyano, acetyl, $CF_3$, $C_2F_5$ or $C_{1-4}$ alkyl, and $R_2$ is hydrogen.

4. A compound according to claim 3 wherein $R_1$ is cyano.

5. A compound according to claim 1 wherein $R_3$ and $R_4$ are both methyl groups.

6. A compound according to claim 1 wherein $R_5$ is hydroxy and $R_6$ is hydrogen and the pyridineamino moiety is trans to $R_5$.

7. A compound according to claim 1 wherein $R_7$ is chloro.

8. A compound selected from the group consisting of:
trans-6-cyano-4-[(6-chloropyrimidin-4-yl)amino]-3,4-dihydro-2,2-dimethyl-2H-1-benzopyran-3-ol;
trans-6-cyano-4-[(6-methylaminopyrimidin-4-yl)amino-3,4-dihydro-2,2-dimethyl-2H-1-benzopyran-3-ol; and
trans-6-cyano-4-[(6-aminopyrimidin-4-yl)amino-3,4-dihydro-2,2-dimethyl-2H-1-benzopyran-3-ol.

9. A pharmaceutical composition for treating disorders associated with smooth muscle contraction of the respiratory system in mammals, comprising an effective amount of a compound according to claim 1, and a pharmaceutically acceptable carrier.

10. A method of treating disorders associated with smooth muscle contraction of the respiratory system in mammals, comprising the administration to mammals of an effective amount of a compound according to claim 1.

* * * * *